(12) United States Patent
Abboud

(10) Patent No.: US 7,049,319 B2
(45) Date of Patent: May 23, 2006

(54) COLON CLEANSING COMPOSITION AND METHOD

(76) Inventor: Semaan Abboud, 109 Heronwood Dr., Milton, DE (US) 19868

( * ) Notice: Subject to any disclaimer, the term of this patent is extended or adjusted under 35 U.S.C. 154(b) by 406 days.

(21) Appl. No.: 10/668,071

(22) Filed: Sep. 23, 2003

(65) Prior Publication Data

US 2005/0064043 A1    Mar. 24, 2005

(51) Int. Cl.
*A61K 33/42* (2006.01)
*A61K 31/166* (2006.01)
*A61K 31/4402* (2006.01)
*A61P 1/10* (2006.01)

(52) U.S. Cl. .................. 514/277; 514/619; 514/867; 514/872; 514/892; 424/601; 424/602; 424/606; 424/680; 424/722

(58) Field of Classification Search ........ 424/601–602, 424/606, 680, 722; 514/277, 619, 867, 872, 514/892

See application file for complete search history.

(56) References Cited

U.S. PATENT DOCUMENTS

| | | | |
|---|---|---|---|
| 4,403,982 A | 9/1983 | Clayton |
| 4,406,655 A | 9/1983 | Clayton |
| 4,975,286 A | 12/1990 | Hechter |
| 5,197,950 A | 3/1993 | Clayton |
| 5,219,573 A | 6/1993 | Tarka, Jr. et al. |
| 5,616,346 A | 4/1997 | Aronchick |
| 5,710,183 A | 1/1998 | Halow |
| 5,858,403 A | 1/1999 | Borody et al. |
| 5,997,906 A | 12/1999 | Wood et al. |
| 6,103,268 A | 8/2000 | Borody et al. |
| 6,132,767 A | 10/2000 | Borody et al. |
| 6,162,464 A | 12/2000 | Jacob et al. |
| 6,235,745 B1 | 5/2001 | Megens |
| 6,444,198 B1 | 9/2002 | Daggy et al. |
| 6,447,763 B1 | 9/2002 | Gordon |
| 2001/0020025 A1 | 9/2001 | Megens |
| 2002/0039400 A1 | 4/2002 | Kaufman et al. |
| 2002/0045153 A1 | 4/2002 | Kaufman et al. |
| 2002/0085990 A1 | 7/2002 | Daggy et al. |
| 2003/0022933 A1 | 1/2003 | Ueno |

OTHER PUBLICATIONS

Drug Facts and Comparisons, Facts and Comparisons, St. Louis, 2002, pp. 1235-1237.*
Medline Abstract, accession No. 1999113696.*
Zmora, O. et al., "Trends in preparation for colorectal surgery..." The American Surgeon, vol. 69(2), pp. 150-154 (Feb. 2003).*
Tasci, I. et al., "Bowel cleansing for diagnostic colonoscopy: which method is preferable? Istanbul experience," Techniques in Coloproctology, vol. 7, pp. 18-21 (2003).*
Toledo, T.K. et al., "Review article: colon cleansing preparation for gastrointestinal procedures," Alimentary Pharmacology & Therapeutics, vol. 15, pp. 605-611 (2001).*
Pinfield, A., "Randomised trial of two pharmacological methods of bowel preparation for day case colonoscopy," Archives of Diseases in Childhood, vol. 80, pp. 181-183 (1999).*

* cited by examiner

*Primary Examiner*—John Pak
(74) *Attorney, Agent, or Firm*—Hall, Vande Sande & Pequignot

(57) ABSTRACT

A composition and method for cleansing a colon prior to endoscopic procedure. More particularly, a combination of bisacodyl, metoclopramide, sodium, and/or a phosphorus containing composition administered in sequential doses for preparing a colon prior to colonoscopy.

8 Claims, No Drawings

COLON CLEANSING COMPOSITION AND METHOD

FIELD OF INVENTION

This invention relates to a composition and method for preparing a colon for an endoscopic procedure. More particularly, this invention relates to a composition and method for cleansing a colon prior to colonoscopy.

BACKGROUND OF INVENTION

Colonoscopy is an endoscopic procedure designed for detecting cancers or polyps of the colon at early stages so that identified cancers can be timely and effectively treated. It is known, for example, that when certain cancers are detected at an early stage, survivability statistics are at their highest.

In order to perform a colonoscopy, a colonoscope is used. A conventional colonoscope, as has been employed in the medical arts for many years, is constructed of a flexible tube containing fiber optics and a miniature CCD (or other type) camera and light located at the tube's distal end. A small lens is employed at the tube end in order to focus light onto the camera.

During a colonoscopy procedure, the distal end of a colonoscope is inserted into the colon and images of the interior walls of the colon are transmitted to a video-screen. In this manner, abnormalities in the colon may be observed and, in certain instances, polyps identified and removed such as for biopsy. Because it is extremely important that the view of the colon walls not be impeded by waste matter, and because the size of the lens of the colonoscope is very small and therefore easily obstructed, it is critical to performing a successful colonoscopy that the colon be thoroughly cleansed prior to the procedure.

For the foregoing reasons, various colon preparation compositions and methods have been employed in the past for cleansing or purging the colon prior to endoscopy. Although many of these compositions and/or methods achieve their intended purpose, known colon preparation procedures are inconvenient and/or uncomfortable to the patient to which they are administered.

For example, a commonly used colon preparation composition is manufactured and sold under the tradename Fleet Phospho-Soda™ (hereinafter Fleet™) In order to achieve the desired result using Fleet™ (sufficient cleansing of the colon), a patient must typically ingest approximately 80 ounces or more of fluids over a relatively short interval of time the day or evening prior to the colonoscopy procedure. Because the ingestion of large volumes of fluid can cause discomfort and, in some instances, nausea or other undesirable symptoms, alternative means to cleanse a colon prior to endoscopy are desired.

In view of the above-enumerated drawbacks, it is apparent that there exists a need in the art for compositions and/or methods for pre-colonoscopy colon preparation which overcome the above drawbacks. It is a purpose of this invention to fulfill these needs in the art, as well as other needs which will become apparent to the skilled artisan once given the above disclosure.

SUMMARY OF INVENTION

Generally speaking, this invention fulfills the above described needs in the art by providing:

a method of cleansing a colon in preparation for a colonoscopy comprising:

ingesting a combination of compositions in pharmaceutically effective amounts, said combination of compositions comprising: bisacodyl, metoclopramide, a phosphorus containing composition, and sodium.

In further embodiments, therein is provided:

a combination of compositions for cleansing a colon prior to a medical examination procedure, the combination of compositions comprising:

a pharmaceutically effective amount of metoclopramide;

a pharmaceutically effective amount of bisacodyl;

a pharmaceutically effective amount of a phosphorus containing composition; and a pharmaceutically effective amount of sodium.

In some embodiments, the combination of compositions is ingested in sequential doses over a multi-day time-period.

In still other embodiments, the sequential doses comprise: a first dose comprising bisacodyl; a second dose comprising a combination of bisacodyl, metoclopramide, a phosphorus containing composition, and sodium; a third dose comprising bisacodyl, a phosphorus containing composition, and sodium; and a fourth dose comprising metoclopramide.

In still further embodiments, the need for consuming large volumes of liquid prior to colonoscopy procedure is eliminated.

DETAILED DESCRIPTION OF CERTAIN EMBODIMENTS

For a more complete understanding of the present invention and advantages thereof, reference is now made to the following description of various illustrative and non-limiting embodiments.

In an exemplar embodiment of the subject invention, pharmaceutically effective amounts of a combination of pharmaceutical compositions are prescribed for oral consumption by a patient. In some preferred embodiments, the compositions are ingested as a series of sequential doses during a time interval of approximately 2–3 days. Although the compositions are preferably administered in tablet or capsule form for ease of consumption, other forms of administration, in similar doses, are of course acceptable (e.g. sachets dissolved in water). It is noted in this regard, however, that one of the primary objectives of the instant invention is the elimination of the need for requiring the consumption of large volumes of liquid. For this reason, tablets or capsules are the most preferred method of administration.

The pharmaceutical compositions which are administered according to the method of the subject invention and/or comprise the combination according to the subject invention are as follows:

Compositions:

I. Common Name: Metoclopramide

Chemical Name: (4-amino-5-chloro-N-[2-(diethylamino) ethyl]-2-methoxy benzamide monohydrochloride monohydrate)

Chemical Formula: $C_{14}H_{22}ClN_3O_2$.

Available under the tradename: Reglan™

II. Common Name: Bisacodyl

Chemical Name: (4,4'-(2-pyridylmethylene) di(phenylacetate))

Chemical Formula: $C_{22}H_{19}NO_4$

Available under the tradename: Dulcolax™

III. Common Name: Phosphate or a phosphate containing composition such as (preferably) potassium phosphate, monobasic sodium phosphate, or dibasic sodium phosphate.

Chemical Formula: $K_xPO_4$ (x=1-3)

Available under the tradename: K-Phos™ or K-Phos-Neutral™ (also containing an appropriate dose ratio of sodium)

IV. Common Name: Sodium

Chemical Symbol: Na

Contained, in the appropriate ratio relative to phosphate, as an ingredient in K-Phos™ or K-Phos-Neutral™.

In preferred embodiments, the compositions are administered according to the following example dosage amounts:

Dosages:

Up to 30 mg of bisacodyl, preferably between 5–30 mg, more preferably between 10–30 mg, and most preferably between 20–30 mg.

Up to 30 mg of metoclopramide, preferably between 5–30 mg, more preferably between 10–30 mg, and most preferably between 20–30 mg.

Up to 3.6 g of potassium phosphate (preferably as K-Phos or K-Phos-Neutral which contains an approximate ratio of phosphate to potassium of 5:1), preferably between 600 mg and 3 g, more preferably between 1.2–3 g, and most preferably between 1.8–3 g.

Up to 3.6 g of sodium (e.g. contained in K-Phos or K-Phos-Neutral), preferably between 600 mg and 3 g, more preferably between 1.2–3 g, and most preferably between 1.8–3 g.

A preferred dosage schedule is set forth below. This schedule is normally provided to patients prior to a colonoscopy procedure and details the manner and amount of the doses as well as when they are to be taken. In this regard, the instructions below are intended for a patient with a procedure scheduled for the afternoon of the third day following the beginning of the cleansing program. Different instructions may, of course, be provided for morning procedures, or variations in the instructions made for other reasons when necessary or simply as desired. The instructions below, however, have proven in practice to be particularly successful for the majority of patients.

Pre-Colonoscopy Dosage Instructions

Day 1

Two days prior to the procedure, the patient is directed to ingest 10 mg of bisacodyl (e.g. 2 Dulcolax™ tablets).

Day 2

One day prior to the procedure, at approximately 8:00 AM, the patient is instructed to take 10 mg of metoclopramide (e.g. 1 Reglan™ tablet), 10 mg of bisacodyl (e.g. 2 Dulcolax™ tablets), and 1.2 g each of potassium phosphate and sodium (e.g. approximately 4 K-Phos-Neutral™ tablets).

After the initial morning dosage, the patient is permitted to drink clear fluids up until three hours prior to the exam. Acceptable clear fluids are:

Water, strained fruit juices without pulp (apple, white grape, lemonade), clear broth or bouillon, coffee or tea (without milk or non-dairy creamer), and Gatorade™, carbonated and non-carbonated soft drinks, Kool-Aid™ or other fruit flavored drinks, plain Jell-O™ without added fruits or toppings, and Popsicles™ as long as none of the above are either red or purple.

At 12:00 Noon, the patient is directed to consume an additional 10 mg of bisacodyl and 1.2 g each of potassium phosphate and sodium (e.g. as commercially available tablets or capsules such as described above).

Note: The day prior to the colonoscopy procedure, the patient is advised not to take any fiber supplements or anti-inflammatories which are not approved in advance by the attending physician.

Day 3: The Day of the Procedure:

In the morning, the patient is instructed to take 10 mg of metoclopramide (e.g. 1 tablet of Reglan™).

The patient is permitted to continue to drink clear fluids until three hours prior to the procedure.

Note: Most normal medications are permitted to be taken but should be discussed first with the physician. If taken, they should be consumed with a small amount of water.

In the above instructions, the use of the term "day" is intended only to represent an approximation of a recognized twenty-four hour time period (i.e. from midnight to midnight). Alternatively, the term "day" may be construed to mean the transition from one twenty-four hour period to another or, further alternatively, a time period of approximately 18–30 hours. For these reasons, the times described herein should not be construed literally or limiting, because variations of these times may be employed to obtain acceptable results. Additionally, dosage amounts are provided only as particularly efficacious examples and should not be construed as restricting the scope of the invention. In this regard, patients having different physiologies and/or body weights will react differently to the various doses of the pharmaceutical compositions described herein and, therefore, the precise amounts that are prescribed thereof should be determined by the physician performing the procedure based on these as well as other factors.

When the above instructions are followed in practice, a cleansing of the colon takes place (e.g. by, in part, inducing peristalsis) which is adequate, in the majority of cases, for a successful colonoscopy to be performed. In this regard, the conditions required for performing a "successful colonoscopy" are defined as cleansing the colon sufficiently such that the interior colon walls may be clearly viewed for accurate diagnosis and such that the camera lens of the colonoscope is not significantly obstructed by food waste matter.

As will be noticed from the foregoing example, throughout a typical dosage schedule, only approximately 14 tablets (or capsules) are required to be ingested. Surprisingly, however, consuming this relatively small number of pills is sufficient to obtain the cleansing necessary to permit successful colonoscopy. In contrast, some prior art colon preparation procedures dictate that upwards of forty pills be consumed over a similar time period. Moreover, the inventive combination of compositions and method for administration thereof does not require that unusual and/or uncomfortable or nauseating volumes of liquids be consumed. For these reasons, the above-enumerated drawbacks of the prior art are avoided.

Once given the above disclosure, many other features, modifications, and improvements will become apparent to the skilled artisan. Such other features, modifications, and improvements are therefore considered to be part of this invention, the scope of which is to be determined by the following claims:

I claim:

1. A method of cleansing a colon in preparation for a colonoscopy comprising ingesting a combination of compositions in pharmaceutically effective amounts, wherein said combination of compositions is ingested in a series of sequential doses comprising:
   a) a first dose comprising bisacodyl;
   b) a second dose comprising a combination of bisacodyl, metoclopramide, a phosphorus containing composition, and sodium;
   c) a third dose comprising bisacodyl, a phosphorus containing composition, and sodium; and
   d) a fourth dose comprising metoclopramide.

2. The method according to claim 1 wherein said second dose is ingested approximately 8–36 hours after said first dose.

3. The method according to claim 2 wherein said third dose is ingested approximately 2–14 hours after said second dose.

4. The method according to claim 3 wherein said fourth dose is ingested approximately 6–14 hours after said third dose.

5. The method according to claim 2 wherein said first dose is ingested approximately two days prior to a colonoscopy procedure.

6. The method according to claim 5 wherein:
   a) said first dose comprises 5–15 mg bisacodyl;
   b) said second dose comprises a combination of 5–15 mg bisacodyl, 5–15 mg metoclopramide, 0.5–2 g of said phosphorus containing composition, and 0.5–2 g sodium;
   c) said third dose comprises 5–15 mg bisacodyl, 0.5–2 g of said phosphorus containing composition, and 0.5–2 g sodium; and
   d) said fourth dose comprises 5–15 mg metoclopramide.

7. The method according to claim 1, wherein said combination of compositions, when ingested by a patient having a colon, is sufficient to trigger a physiological response, including peristalsis of the colon, whereby the colon is subsequently adequately cleansed for a colonoscopy procedure.

8. The method according to claim 1, wherein said phosphorus containing composition is selected from the group consisting of phosphate, potassium phosphate, monobasic sodium phosphate, and dibasic sodium phosphate.

* * * * *